United States Patent
Prest et al.

(10) Patent No.: US 7,820,890 B1
(45) Date of Patent: Oct. 26, 2010

(54) INBRED CORN LINE G07-NPXA6496

(75) Inventors: Tom Prest, Ames, IA (US); Allen Brush, Ainsworth, IA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 12/072,742

(22) Filed: Feb. 28, 2008

Related U.S. Application Data

(60) Provisional application No. 60/904,640, filed on Mar. 1, 2007.

(51) Int. Cl.
- *A01H 1/00* (2006.01)
- *C07H 21/04* (2006.01)
- *C07K 14/415* (2006.01)
- *C12N 15/00* (2006.01)

(52) U.S. Cl. .................... 800/320.1; 435/468; 435/412; 435/418; 435/424; 530/370; 536/23.1; 800/260; 800/278; 800/303

(58) Field of Classification Search ................. 435/69.1, 435/468, 412, 419, 320.1; 530/370; 536/23.6; 800/278, 295, 320.1
See application file for complete search history.

(56) References Cited

U.S. PATENT DOCUMENTS

| 6,706,955 | B2 | 3/2004 | Miller | |
|---|---|---|---|---|
| 7,235,725 | B1 * | 6/2007 | Weyhrich | ................ 800/320.1 |

OTHER PUBLICATIONS

PVP certificate 9800319 filed Jun. 11, 1998 issued Apr. 21, 2000.

* cited by examiner

*Primary Examiner*—Phuong T Bui
(74) *Attorney, Agent, or Firm*—Dana Rewoldt

(57) ABSTRACT

Basically, this invention provides for an inbred corn line designated G07-NPXA6496, methods for producing a corn plant by crossing plants of the inbred line G07-NPXA6496 with plants of another corn plants. The invention relates to the various parts of inbred G07-NPXA6496 including culturable cells. This invention also relates to methods for introducing transgenic transgenes into inbred corn line G07-NPXA6496 and plants produced by said methods.

19 Claims, No Drawings

INBRED CORN LINE G07-NPXA6496

REFERENCE TO RELATED APPLICATION

This application claims the benefit under Title 35, United States Code, §119(e) of U.S. provisional application 60/904,640 filed Mar. 1, 2007.

FIELD OF THE INVENTION

This invention is in the field of corn breeding, specifically relating to an inbred corn line designated G07-NPXA6496. This invention also is in the field of hybrid maize production employing the present inbred.

BACKGROUND OF THE INVENTION

The original maize plant was indigenous to the Western Hemisphere. The plants were weed like and only through the efforts of early breeders were cultivated crop species developed. The crop cultivated by early breeders, like the crop today, could be wind pollinated. The physical traits of maize are such that wind pollination results in self-pollination or cross-pollination between plants. Each maize plant has a separate male and female flower that contributes to pollination, the tassel and ear, respectively. Natural pollination occurs when wind transfers pollen from tassel to the silks on the corn ears. This type of pollination has contributed to the wide variation of maize varieties present in the Western Hemisphere.

The development of a planned breeding program for maize only occurred in the last century. A large part of the development of the maize product into a profitable agricultural crop was due to the work done by land grant colleges. Originally, maize was an open pollinated variety having heterogeneous genotypes. The maize farmer selected uniform ears from the yield of these genotypes and preserved them for planting the next season. The result was a field of maize plants that were segregating for a variety of traits. This type of maize selection led to Summary of the G07-NPXA6496 incremental increases in seed yield.

Large increases in seed yield were due to the work done by land grant colleges that resulted in the development of numerous hybrid corn varieties in planned breeding programs. Hybrids were developed from inbreds which were developed by selecting corn lines and selfing these lines for several generations to develop homozygous pure inbred lines. One selected inbred line was emasculated and another selected inbred line pollinated the emasculated inbred to produce hybrid seed F1 on the emasculated inbred line. Emasculation of the inbred usually is done by detasseling the seed parent; however, emasculation can be done in a number of ways. For example an inbred could have a male sterility factor which would eliminate the need to detassel the inbred.

In the early seventies the hybrid corn industry attempted to introduce CMS (cytoplasmic male sterility) into a number of inbred lines. Unfortunately, the CMS inbreds also introduced some very poor agronomic performance traits into the hybrid seed which caused farmers concern causing the maize industry to shy away from CMS material for a couple of decades thereafter.

However, in the last 10-15 years a number of different male sterility systems for maize have been successfully deployed. The most traditionally of these male sterility and/or CMS systems for maize parallel the CMS type systems that have been routinely used in hybrid production in sunflower.

In the standard CMS system there are three different maize lines required to make the hybrid. First, there is a cytoplasmic male-sterile line usually carrying the CMS or some other form of male sterility. This line will be the seed producing parent line. Second, there must be a fertile inbred line that is the same or isogenic with the seed producing inbred parent but lacking the trait of male sterility. This is a maintainer line needed to make new inbred seed of the seed producing male sterile parent. Third there is a different inbred which is fertile, has normal cytoplasm and carries a fertility restoring gene. This line is called the restorer line in the CMS system. The CMS cytoplasm is inherited from the maternal parent (or the seed producing plant); therefore for the hybrid seed produced on such plant to be fertile the pollen used to fertilize this plant must carry the restorer gene. The positive aspect of this is that it allows hybrid seed to be produced without the need for detasseling the seed parent. However, this system does require breeding of all three types of lines: 1) male sterile-to carry the CMS: 2) the maintainer line; and, 3) the line carrying the fertility restorer gene. Use of a switchable male sterility gene reduces the complexity of the sterility system.

In other instances, sterile hybrids are produced and the pollen necessary for the formation of grain on these hybrids is supplied by interplanting of fertile inbreds in the field with the sterile hybrids.

Whether the seed producing plant is emasculated due to detasseling or CMS or transgenes, the seed produced by crossing two inbreds in this manner is hybrid seed. This hybrid seed is F1 hybrid seed. The grain produced by a plant grown from a F1 hybrid seed is referred to as F2 or grain. Although, all F1 seed and plants, produced by this hybrid seed production system using the same two inbreds should be substantially the same, all F2 grain produced from the F1 plant will be segregating maize material.

The hybrid seed production produces hybrid seed which is heterozygous. The heterozygosis results in hybrid plants, which are robust and vigorous plants. Inbreds on the other hand are mostly homozygous. This homozygosity renders the inbred lines less vigorous. Inbred seed can be difficult to produce since the inbreeding process in corn lines decreases the vigor. However, when two inbred lines are crossed, the hybrid plant evidences greatly increased vigor and seed yield compared to open pollinated, segregating maize plants. An important consequence of the homozygosity and the homogeneity of the inbred maize lines is that all hybrid seed produced from any cross of two such elite lines will be the same hybrid seed and make the same hybrid plant. Thus the use of inbreds makes hybrid seed which can be reproduced readily.

The ultimate objective of the commercial maize seed companies is to produce high yielding, agronomically sound plants that perform well in certain regions or areas of the Corn Belt. To produce these types of hybrids, the companies must develop inbreds, which carry needed traits into the hybrid combination. Hybrids are not often uniformly adapted for the entire Corn Belt, but most often are specifically adapted for regions of the Corn Belt. Northern regions of the Corn Belt require shorter season hybrids than do southern regions of the Corn Belt. Hybrids that grow well in Colorado and Nebraska soils may not flourish in richer Illinois and Iowa soils. Thus, a variety of major agronomic traits is important in hybrid combination for the various Corn Belt regions, and has an impact on hybrid performance.

Inbred line development and hybrid testing have been emphasized in the past half-century in commercial maize production as a means to increase hybrid performance. Inbred development is usually done by pedigree selection. Pedigree selection can be selection in an F2 population produced from a planned cross of two genotypes (often elite inbred lines), or selection of progeny of synthetic varieties, open pollinated, composite, or backcrossed populations. This type of selection is effective for highly inheritable traits, but other traits, for example, yield requires replicated test crosses at a variety of stages for accurate selection.

Maize breeders select for a variety of traits in inbreds that impact hybrid performance along with selecting for acceptable parental traits. Such traits include: yield potential in hybrid combination; dry down; maturity; grain moisture at harvest; greensnap; resistance to root lodging; resistance to stalk lodging; grain quality; disease and insect resistance; ear and plant height. Additionally, hybrid performance will differ in different soil types such as low levels of organic matter, clay, sand, black, high pH, low pH; or in different environments such as wet environments, drought environments, and no tillage conditions. These traits appear to be governed by a complex genetic system that makes selection and breeding of an inbred line extremely difficult. Even if an inbred in hybrid combination has excellent yield (a desired characteristic), it may not be useful because it fails to have acceptable parental traits such as seed yield, seed size, pollen production, good silks, plant height, etc.

To illustrate the difficulty of breeding and developing inbred lines, the following example is given. Two inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. In addition, most traits in the corn genome are regrettably not single dominant genes but are multi-genetic with additive gene action not dominant gene action. Thus, the general procedure of producing a non segregating F1 generation and self pollinating to produce a F2 generation that segregates for traits and selecting progeny with the visual traits desired does not easily lead to an useful inbred. Great care and breeder expertise must be used in selection of breeding material to continue to increase yield and the agronomics of inbreds and resultant commercial hybrids.

Certain regions of the Corn Belt have specific difficulties that other regions may not have. Thus the hybrids developed from the inbreds have to have traits that overcome or at least minimize these regional growing problems. Examples of these problems include in the eastern corn belt Gray Leaf Spot, in the north cool temperatures during seedling emergence, in the Nebraska region CLN (Corn Lethal Necrosis) and in the west soil that has excessively high pH levels. The industry often targets inbreds that address these issues specifically forming niche products. However, the aim of most large seed producers is to provide a number of traits to each inbred so that the corresponding hybrid can be useful in broader regions of the Corn Belt. The new biotechnology techniques such as Microsatellites, RFLPs, RAPDs and the like have provided breeders with additional tools to accomplish these goals.

The present invention relates to an inbred corn line G07-NPXA6496. Specifically, this invention relates to plants and seeds of this line. Additionally, this relates to a method of producing from this inbred, hybrid seed corn and hybrid plants with seeds from such hybrid seed. More particularly, this invention relates to the unique combination of traits that combine in corn line G07-NPXA6496.

Generally then, broadly the present invention includes an inbred corn seed designated G07-NPXA6496. This seed produces a corn plant.

The invention also includes the tissue culture of regenerable cells of G07-NPXA6496 wherein the cells of the tissue culture regenerates plants capable of expressing the genotype of G07-NPXA6496. The tissue culture is selected from the group consisting of leaf, pollen, embryo, root, root tip, guard cell, ovule, seed, anther, silk, flower, kernel, ear, cob, husk and stalk, cell and protoplast thereof. The corn plant regenerated from G07-NPXA6496 or any part thereof is included in the present invention. The present invention includes regenerated corn plants that are capable of expressing G07-NPXA6496's genotype, phenotype or mutants or variants thereof.

The invention extends to hybrid seed produced by planting, in pollinating proximity which includes using preserved maize pollen as explained in U.S. Pat. No. 5,596,838 to Greaves, seeds of corn inbred lines G07-NPXA6496 and another inbred line if preserved pollen is not used; cultivating corn plants resulting from said planting; preventing pollen production by the plants of one of the inbred lines if two are employed; allowing cross pollination to occur between said inbred lines; and harvesting seeds produced on plants of the selected inbred. The hybrid seed produced by hybrid combination of plants of inbred corn seed designated G07-NPXA6496 and plants of another inbred line are apart of the present invention. This inventions scope covers hybrid plants and the plant parts including the grain and pollen grown from this hybrid seed.

The invention further includes a method of hybrid F1 production. A first generation (F1) hybrid corn plant produced by the process of planting seeds of corn inbred line G07-NPXA6496; cultivating corn plants resulting from said planting; permitting pollen from another inbred line to cross pollinate inbred line G07-NPXA6496; harvesting seeds produced on plants of the inbred; and growing a harvested seed are part of the method of this invention.

The present invention also encompasses a method of introducing at least one targeted trait into maize inbred line comprising the steps of: (a) crossing plant grown from the present invention seed which is the recurrent parent, representative seed of which has been deposited, with the donor plant of another maize line that comprises at least one target trait selected from the group consisting of male sterility, herbicide resistance, insect resistance, disease resistance, amylose starch, and waxy starch to produce F1 plants; (b) selecting from the F1 plants that have at least one of the targeted traits, forming a pool of progeny plants with the targeted trait; (c) crossing the pool of progeny plants with the present invention which is the recurrent parent to produce backcrossed progeny plants with the targeted trait; (d) selecting for backcrossed progeny plants that have at least one of the target traits and physiological and morphological characteristics of maize inbred line of the recurrent parent, listed in Table 1 as traits of the present invention forming a pool of selected backcrossed progeny plants; and (e) crossing the selected backcrossed progeny plants to the recurrent parent and selecting from the resulting plants for the targeted trait and physiological and morphological characteristics of maize inbred line of the recurrent parent, listed in Table 1 and reselecting from the pool of resulting plants and repeating the crossing to the recurrent parent and selecting step in succession to form a plant that comprise the desired trait and all of the physiological and morphological characteristics of maize inbred line of the recurrent parent if the present invention listed in Table 1 as determined at the 5% significance level when grown in the same environmental conditions.

This method and the following method of introducing traits can be done with less back crossing events if the trait and/or the genotype of the present invention are selected for or identified through the use of markers. SSR, microsatellites, SNP and the like decrease the amount of breeding time required to locate a line with the desired trait or traits and the characteristics of the present invention. Backcrossing in two or even three traits (for example the glyphosate, Europe corn borer, corn rootworm resistant genes) is routinely done with the use of marker assisted breeding techniques. This introduction of transgenes or mutations into a maize line is often called single gene conversion. Although, presently more than one gene particularly transgenes or mutations which are readily tracked with markers can be moved during the same "single gene conversion" process, resulting in a line with the addition of more targeted traits than just the one, but still having the characteristics of the present invention plus those characteristics added by the targeted traits.

The method of introducing a desired trait into maize inbred line comprising: (a) crossing plant grown from the present invention seed, representative seed of which has been deposited the recurrent parent, with plant of another maize line that comprises at least one target trait selected from the group consisting of nucleic acid encoding an enzyme selected from the group consisting of phytase, stearyl-ACP desaturase, fructosyltransferase, levansucrase, amylase, invertase, starch synthase, branching enzyme, and debranching enzyme, and starch branching enzyme, the donor parent to produce F1 plants; (b) selecting for the targeted trait from the F1 plants, forming a pool of progeny plants; (c) crossing the progeny plants with the recurrent parent to produce backcrossed progeny plants; (d) selecting for backcrossed progeny plants that have at least one of the target, trait and physiological and morphological characteristics of maize inbred line of the present invention as listed in Table 1 for the invention forming a pool of backcrossed progeny plants; and repeating a step of crossing the new pool with the recurrent parent and selecting for the targeted trait and the recurrent parents characteristics until the selected plant is essentially the recurrent parent with the targeted trait or targeted traits. This selection and crossing may take at least 4 backcrosses if marker assisted breeding is not employed.

The inbred line and seed of the present invention are employed to carry the agronomic package into the hybrid. Additionally, the inbred line is often carrying transgenes that are introduced in to the hybrid seed.

Likewise included is a first generation (F1) hybrid corn plant produced by the process of planting seeds of corn inbred line G07-NPXA6496; cultivating corn plants resulting from said planting; permitting pollen from inbred line G07-NPXA6496 to cross pollinate another inbred line; harvesting seeds produced on plants of the inbred; and growing a plant from such a harvested seed.

A number of different techniques exist which are designed to avoid detasseling in maize hybrid production. Some examples are switchable male sterility, lethal genes in the pollen or anther, inducible male sterility, male sterility genes with chemical restorers. There are numerous patented means of improving upon the hybrid production system. Some examples include U.S. Pat. No. 6,025,546, which relates to the use of tapetum-specific promoters and the barnase gene to produce male sterility; and U.S. Pat. No. 6,627,799 relates to modifying stamen cells to provide male sterility. Therefore, one aspect of the current invention concerns the present invention comprising one or more gene(s) capable of restoring male fertility to male-sterile maize inbreds or hybrids and/or genes or traits to produce male sterility in maize inbreds or hybrids.

The inbred corn line G07-NPXA6496 and at least one transgenic gene adapted to give G07-NPXA6496 additional and/or altered phenotypic traits are within the scope of the invention. Such transgenes are usually associated with regulatory elements (promoters, enhancers, terminators and the like). Presently, transgenes provide the invention with traits such as insect resistance, herbicide resistance, disease resistance increased or deceased starch or sugars or oils, increased or decreased life cycle or other altered trait.

The present invention includes inbred corn line G07-NPXA6496 and at least one transgenic gene adapted to give G07-NPXA6496 modified starch traits. Furthermore this invention includes the inbred corn line G07-NPXA6496 and at least one mutant gene adapted to give modified starch, acid or oil traits, i.e. amylase, waxy, amylose extender, starch synthase (SS) SSI, SSIIa, SSIIIa, SSIIIb, SSIVa, SSIVb, branching enzyme (BE), BEI, BEIIa, BEIIb, debranching enzyme, surgary 1, or amylose. The present invention includes the inbred corn line G07-NPXA6496 and at least one transgenic gene: *bacillus thuringiensis*, the bar or pat gene encoding Phosphinothricin acetyl Transferase, Gdha gene, GOX, VIP, EPSP synthase gene, low phytic acid producing gene, and zein. The inbred corn line G07-NPXA6496 and at least one transgenic gene useful as a selectable marker or a screenable marker is covered by the present invention.

A tissue culture of the regenerable cells of hybrid plants produced with use of G07-NPXA6496 genetic material is covered by this invention. A tissue culture of the regenerable cells of the corn plant produced by the method described above is also included.

DEFINITIONS

In the description and examples, which follow, a number of terms are used. In order to provide a clear and consistent understanding of the specifications and claims, including the scope to be given such terms, the following definitions are provided.

Early Season Trait Codes

Emergence (EMRGR): Recorded when 50% of the plots in the trial are at V1 (1 leaf collar) growth stage.

1=All plants have emerged and are uniform in size

3=All plants have emerged but are not completely uniform

5=Most plants have emerged with some just beginning to break the soil surface, noticeable lack of uniformity 7=Less than 50% of the plants have emerged, and lack of uniformity is very noticeable 9=A few plants have emerged but most remain under the soil surface.

Seedling Growth (SVGRR): Recorded between V3 and V5 (3-5 leaf stage) giving greatest weight to seedling plant size and secondary weight to uniform growth. 1=Large plant size and uniform growth 3=Acceptable plant size and uniform growth 5=Acceptable plant size and might be a little non-uniform 7=Weak looking plants and non-uniform growth 9=Small plants with poor uniformity When taking emergence notes, hybrid ratings are relative to each other over the trial.

Purpling (PRPLR): Emergence and/or early growth rating. Purpling is more pronounced on the under sides of leaf blades especially on midribs.

1=No plants showing purple color

3=30% plants showing purple color

5=50% plants showing purple color

7=70% plants showing purple color

9=90+% plants showing purple color

Herbicide Injury (HRBDR) List the herbicide type, which is being rated. Then rated each hybrid/variety injury as indicated below.

1=No apparent reduction in biomass or other injury symptoms

5=Moderate reduction in biomass with some signs of sensitivity

9=Severe reduction in biomass with some mortality

Mid-Season Traits Codes

Heat Units to 50% Silk (HUPSN): Recorded the day when 50% of all plants within a plot show 2 cm or more silk protruding from the ear. Converted days to accumulated heat units from planting.

Heat units to 50% Pollen Shed (HUPSN): Recorded the day when 50% of all plants within a plot are shedding pollen. Converted days to accumulated heat units from planting.

Plant Height in cm (ERHTN): After pollination, recorded average plant height of each plot. Measured from ground to base of leaf node. Three or more locations recorded.

Plant Ear Height in cm (PLHTN): After pollination, recorded average ear height of each plot. Measured from ground to base of ear node (shank). Three or more locations should be recorded.

Root Lodging Early % (ERTLP): Early root lodging occurs up to about two weeks after flowering and usually involves goosenecking. Counted the number of root lodged plants and converted to percentage. For Field Evaluation Test plots (FET), recorded lodged plants out of 50 plants from two locations in each hybrid strip, sum, and record percentage.

Foliar Disease (LFDSR): Foliar disease ratings taken one month before harvest through harvest. The predominant disease should be listed in the trial information and individual hybrid ratings are recorded.

1=No lesions to two lesions per leaf.

3=A few scattered lesions on the leaf. About five to ten percent of the leaf surface is affected.

5=A moderate number of lesions are on the leaf. About 15 to 20 percent of the leaf surface is affected.

7=Abundant lesions are on the leaf. About 30 to 40 percent of the leaf surface is affected.

9=Highly abundant lesions (>50 percent) on the leaf. Lesions are highly coalesced. Plants may be prematurely killed.

Data collection (as described above) on the following diseases:

Common Rust (CR) Eye Spot (ES)

Gray Leaf Spot (GLS) Northern Corn Leaf Blight (NCLB)

Stewart's Bacterial Wilt (SBW) Southern Corn Leaf Blight (SCLB)

Southern Rust (SR) Corn Virus Complex (CVC)

Preharvest Trait Codes

Heat units to Black Layer (HUBLN): Recorded the day when 50% of all plants within a plot reach black layer stage. Converted days to accumulated heat units from planting. Taken on border rows of four-row plots.

Harvest Population (HAVPN): Counted the number of plants in yield rows, excluding tillers, in each plot. For FET plots, count a thousandth of an acre two times and record the average.

Barren Plants (BRRNP): Counted the number of plants in yield rows having no ears and/or abnormal ears with less than 50 kernels. For FET plots, counted barren plants out of 50 from two locations in each hybrid strip, sum, and record the percentage. Data collected on entire trial.

Dropped Ears (DROPP): Counted the numbers of ears lying on the ground in yield rows.

For FET plots, count dropped ears from the area of 50 plants from two locations in each hybrid strip, sum, and record the percentage.

Stalk Lodging % (STKLP): Stalk lodging will be reported as number of plants broken below the ear without pushing, excluding green snapped plants. Record trials with approximately five percent or more average stalk lodging. Counted the number of broken plants in yield rows and converted to percent. For FET plots, counted stalk lodged plants out of 50 from two locations in each hybrid strip, sum, and recorded the percentage.

Root Lodging Late % (LRTLP): Late root lodging can usually start to occur about two weeks after flowering and involves lodging at the base of the plant. Plants leaning at a 30-degree angle or more from the vertical are considered lodged. Counted the number of root lodged plants in yield rows and converted to percent. For FET plots, counted root lodged plants out of 50 from two locations in each hybrid strip, sum, and record the percentage.

Push Test for Stalk and Root Quality on Erect Plants % (PSTSP): The push test is applied to trials with approximately five percent or less average stalk lodging. Plants are pushed that are not root lodged or broken prior to the push test. Standing next to the plant, the hand is placed at the top ear and pushed to arm's length. Push one of the border rows (four-row small plot) into an adjacent plot border row. Counted the number of plants leaning at a 30-degree angle or more from the vertical, including plants with broken stalks prior to pushing, did not count plants that have strong rinds that snap rather than bend over easily. For FET plots, push 50 plants from two interior locations of each hybrid strip, sum, and record the percentage. The goal of the push test is to identify stalk rot and stalk lodging potential, NOT ECB injury.

Data may be collected in the following manner:

PUSXN: Push ten plants and enter the number of plants that do not remain upright. SPIRIT will calculate PSTSP.

PSTSP: This is a percent. If you push 10 plants you can simply enter 10 times the number of plants that do not remain upright (i.e. 2=20) to get the percentage.

Intactness (INTLR):

1=Healthy appearance, tops unbroken

5=25% of tops broken

9=majority of tops broken

Plant Appearance (PLTAR): This is a visual rating based on general plant appearance taking into account all factors of intactness, pest, and disease pressure.

1=Complete plant with healthy appearance

5=plants look OK

9=Plants not acceptable

Green Snap (GRSNP): Counted the number of plants in yield rows that snapped below the ear due to brittleness associated with high winds. For FET plots, count snapped plants out of 50 from two locations in each hybrid strip, sum, and record the percentage.

Stay-green (STGRP): This is an assessment of the ability of a grain hybrid to retain green color as maturity approaches (taken near the time of black-layer) and should not be a reflection of hybrid maturity or leaf disease. Recorded % of green tissue. This may be listed as a Stay Green Rating instead of a Percentage.

Stay Green Rating (STGRR): This is an assessment of the ability of a grain hybrid to retain green color as maturity approached (taken near the time of black layer or if major differences are noted later). This rating should not be a reflection of the hybrid maturity or leaf disease.

1=solid Green Plant

9=no green tissue

Ear/Kernel Rots (KRDSR): If ear or kernel rots are present, husk ten consecutive ears in each plot and count the number that have evidence of ear or kernel rots, multiply by 10, and round up to the nearest rating as described below. Identify and recorded the disease primarily responsible for the rot.

1=No rots, 0% of the ears infected.

3=Up to 10% of the ears infected.

5=11 to 20% of the ears infected.

7=21 to 35% of the ears infected.

9=36% or more of the ears infected.

Grain Quality (GRQUR): Husked back several ears after black layer stage and observed kernel cap integrity and relative amount of soft starch endosperm along the sides of kernels.

1=smooth kernel caps and or 10% or less soft starch

3=slight kernel wrinkles and or 30% soft starch

7=moderate kernel wrinkles and or 70% soft starch

9=severe kernel wrinkled and or 90% or more soft starch

Preharvest Hybrid Characteristics

Ear Shape Slender, Semi-Blocky, Blocky

DESHR:

1=Blocky

5=Semi-blocky

9=Slender

DROP

Ear Type: Fixed, Semi-Fixed, Flex (Thin outside row, every other plant for half of row.)

EARFR:

1=Flex

5=Semi-flex

9=Fixed

Husk Cover: Short, Medium, Long

HSKCR:

1=Long

5=Medium

9=Short

Kernel Depth: Shallow, Medium, Deep

KRLNR:

1=Deep

5=Medium

9=Short (shallow)

Shank Length: Short, Medium, Long

SHLNR:

1=Short

5=Medium

9=Long

Cob Color (COBCR):

1=White

5=Pink

9=Dark Red

Kernel Row Number: Enter average of 3 ears (KRRWN): The average number of kernel rows on 3 ears.

Cob diameter (COBDR): Cob diameter to be taken with template.

1: small

5: Medium

9: Large

Corn: Harvest Trait Codes

The following are harvest codes:

Number of Rows Harvested (NRHAN); Plot Width (RWIDN); Plot Length (RLENN); Yield Lb/Plot (GWTPN); Test Weight in Lb/Bu (TSTWN); Moisture % (MST_P); Adjusted Yield in Bu/A (YBUAN)—entered or calculated, and Yield in Bushels per acre at standard moisture (YGSMN).

| Color Choices: | | | | | |
|---|---|---|---|---|---|
| 1. | light green | 10. | pink-orange | 19. | white |
| 2. | medium green | 11. | pink | 20. | white capped |
| 3. | dark green | 12. | light red | 21. | buff |
| 4. | very dark green | 13. | cherry red | 22. | tan |
| 5. | green-yellow | 14. | red | 23. | brown |
| 6. | pale yellow | 15. | red and white | 24. | bronze |
| 7. | yellow | 16. | pale purple | 25. | variegated (describe) |
| 8. | yellow-orange | 17. | purple | 26. | other (describe) |
| 9. | salmon | 18. | colorless | | |

-continued

| Form # | ABR. | Description | Input Value |
|---|---|---|---|
| A1 | EMRGN | Final number of plants per plot | # |
| A2 | REGNN | Region Developed: 1.Northwest 2.Northcentral 3.Northeast 4.Southeast 5.Southcentral 6.Southwest 7.Other | # |
| A3 | CRTYN | Cross type: 1.sc 2.dc 3.3w 4.msc 5.m3w 6.inbred 7.rel. line 8.other | # |
| A4 | KRTPN | Kernel type: 1.sweet 2.dent 3.flint 4.flour 5.pop 6.ornamental 7.pipecorn 8.other | # |
| A5 | EMERN | Days to Emergence EMERN | #Days |
| B1 | ERTLP | % Root lodging: (before anthesis): | #% |
| B2 | GRSNP | % Brittle snapping: (before anthesis): | #% |
| C1 | TBANN | Tassel branch angle of 2nd primary lateral branch (at anthesis): | degree |
| C10 | HUPSN | Heat units to 50% pollen shed: (from emergence) | #HU |
| C11 | SLKCN | Silk color: | #/Munsell value |
| C12 | HU5SN | Heat units to 50% silk: (from emergence) | #HU |
| C13 | DSAZN | Days to 50% silk in adapted zone: | #Days |
| C14 | HU9PN | Heat units to 90% pollen shed: (from emergence) | #HU |
| C15 | HU19N | Heat units from 10% to 90% pollen shed: | #HU |
| C16 | DA19N | Days from 10% to 90% pollen shed: | #Days |
| C2 | LSPUR | Leaf sheath pubescence of second leaf above the ear (at anthesis) 1-9 (1 = none): | # |
| C3 | ANGBN | Angle between stalk and 2nd leaf above the ear (at anthesis): | degree |
| C4 | CR2LN | Color of 2nd leaf above the ear (at anthesis): | #/Munsell value |
| C5 | GLCRN | Glume Color: | #/Munsell value |
| C6 | GLCBN | Glume color bars perpendicular to their veins (glume bands): 1.absent 2.present | # |
| C7 | ANTCN | Anther color: | #/Munsell value |
| C8 | PLQUR | Pollen Shed: 1-9 (0 = male sterile) | # |
| C9 | HU1PN | Heat units to 10% pollen shed: (from emergence) | #HU |
| D1 | LAERN | Number of leaves above the top ear node: | # |
| D10 | LTBRN | Number of lateral tassel branches that originate from the central spike: | # |
| D11 | EARPN | Number of ears per stalk: | # |
| D12 | APBRR | Anthocyanin pigment of brace roots: 1.absent 2.faint 3.moderate 4.dark | # |
| D13 | TILLN | Number of tillers: | # |
| D14 | HSKCN | Husk color 25 days after 50% silk: (fresh) | #/Munsell value |
| D2 | MLWVR | Leaf marginal waves: 1-9 (1 = none) | # |
| D3 | LFLCR | Leaf longitudinal creases: 1-9 (1 = none) | # |
| D4 | ERLLN | Length of ear leaf at the top ear node: | #cm |
| D5 | ERLWN | Width of ear leaf at the top ear node at the widest point: | #cm |
| D6 | PLHTN | Plant height to tassel tip: | #cm |
| D7 | ERHCN | Plant height to the top ear node: | #cm |
| D8 | LTEIN | Length of the internode between the ear node and the node above: | #cm |
| D9 | LTASN | Length of the tassel from top leaf collar to tassel tip: | #cm |
| E1 | HSKDN | Husk color 65 days after 50% silk: (dry) | #/Munsell value |
| E10 | DSGMN | Days from 50% silk to 25% grain moisture in adapted zone: | #Days |
| E11 | SHLNN | Shank length: | #cm |
| E12 | ERLNN | Ear length: | #cm |
| E13 | ERDIN | Diameter of the ear at the midpoint: | #mm |
| E14 | EWGTN | Weight of a husked ear: | #gm |
| E15 | KRRWR | Kernel rows: 1.indistinct 2.distinct | # |
| E16 | KRNAR | Kernel row alignment: 1.straight 2.slightly curved 3.curved | # |
| E17 | ETAPR | Ear taper: 1.slight 2.average 3.extreme | # |
| E18 | KRRWN | Number of kernel rows: | # |
| E19 | COBCN | Cob color: | #/Munsell value |
| E2 | HSKTR | Husk tightness 65 days after 50% silk: 1-9 (1 = loose) | # |
| E20 | COBDN | Diameter of the cob at the midpoint: | #mm |
| E21 | YBUAN | Yield: | #kg/ha |

-continued

| | | | |
|---|---|---|---|
| E22 | KRTEN | Endosperm type: 1.sweet 2.extra sweet 3.normal 4.high amylose 5.waxy 6.high protein 7.high lysine 8.super sweet 9.high oil 10.other | 3 |
| E23 | KRCLN | Hard endosperm color: | #/Munsell value |
| E24 | ALECN | Aleurone color: | #/Munsell value |
| E25 | ALCPR | Aleurone color pattern: 1.homozygous 2.segregating | # |
| E26 | KRLNN | Kernel length: | #mm |
| E27 | KRWDN | Kernel width: | #mm |
| E28 | KRDPN | Kernel thickness: | #mm |
| E29 | K1KHN | 100 kernel weight: | #gm |
| E3 | HSKCR | Husk extension: 1.short (ear exposed) 2.medium (8 cm) 3.long (8-10 cm) 4.very long (>10 cm) | # |
| E30 | KRPRN | % round kernels on 13/64 slotted screen: | #% |
| E4 | HEPSR | Position of ear 65 days after 50% silk: 1.upright 2.horizontal 3.pendent | # |
| E5 | STGRP | Staygreen 65 days after anthesis: 1-9 (1 = worst) | # |
| E6 | DPOPP | % dropped ears 65 days after anthesis: | % |
| E7 | LRTRP | % root lodging 65 days after anthesis: | % |
| E8 | HU25N | Heat units to 25% grain moisture: (from emergence) | #HU |
| E9 | HUSGN | Heat units from 50% silk to 25% grain moisture in adapted zone: | #HU |

DETAILED DESCRIPTION OF THE INVENTION

The inbred provides uniformity and stability within the limits of environmental influence for traits as described in the Variety Description Information for the invention listed in Table 1 that follows.

The inbred has been produced through a dihaploid system or is self-pollinated for a sufficient number of generations to give inbred uniformity. During plant selection in each generation, the uniformity of plant type was selected to ensure homozygosity and phenotypic stability. The line has been increased in isolated farmland environments with data on uniformity and agronomic traits being observed to assure uniformity and stability. No variant traits have been observed or are expected in G07-NPXA6496.

The best method of producing the invention is by planting the seed of G07-NPXA6496 which is substantially homozygous and self-pollinating or sib pollinating the resultant plant in an isolated environment, and harvesting the resultant seed.

TABLE 1

G07-NPXA6496
VARIETY DESCRIPTION INFORMATION

1 Type: Dent
2 Region Best Adapted: Broadly adapted

| MG Group | Maturity Range | Hybrid RM (estimate) |
|---|---|---|
| 6 | 108-112 | 114 |

3 Plant Traits

| Syngenta Code | Type | Anther Color | Glume Color | Silk Color | Brace Root Color |
|---|---|---|---|---|---|
| NP2115 | Dent | Yellow/green | Green | Red/purple | |
| G07-NPXA6496 | Dent | Red/purple | Green | Yellow w/ color | Absent and Moderate |
| NP2276 | Dent | Yellow | Green | Yellow | Moderate |

| Syngenta Code | Cob Color | Kernel Color | Endosperm Type |
|---|---|---|---|
| NP2115 | Red | Yellow | Normal |
| G07-NPXA6496 | Red | Yellow | Normal |
| NP2276 | Red | Yellow | |

Plant Disease Data

| Line | GW | EYE | NLB | SLB | GLS |
|---|---|---|---|---|---|
| NP2115 | 8 | 6 | 7 | 5 | 4 |
| G07-NPXA6496 | 3 | 7 | 9 | 6 | 4 |

The data provided above is often a color. The Munsell code is a reference book of color, which is known and used in the industry and by persons with ordinary skill in the art of plant breeding. The purity and homozygosity of inbred G07-NPXA6496 is constantly being tracked using isozyme genotypes.

Isozyme Genotypes for G07-NPXA6496

Isozyme data were generated for inbred corn line G07-NPXA6496 according to procedures known and published in the art. The data in Table 2 gives the electrophoresis data on G07-NPXA6496.

TABLE 2

ELECTROPHORESIS RESULTS FOR G07-NPXA6496

| Line Code | IDH2 | PGD2 | ACP4 | MDH4 | MDH2 | MDH5 | MDH1 | MDH3 | PGM1 |
|---|---|---|---|---|---|---|---|---|---|
| G07-NPXA6496 | 6 | 5 | 3 | 12 | 6 | 12 | 6 | 16 | 9 |
| NP2276 | 6 | 5 | 4 | 12 | 6 | 12 | 6 | 16 | 9 |

| Line Code | MDH6 | PGM2 | PGD1 | PHI1 | IDH1 | AHD1 | PUR % | ACP1 |
|---|---|---|---|---|---|---|---|---|
| G07-NPXA6496 | Mm | 4 | 2(2-3.8) | 4 | 4 | 4 | 99.5 | 2 |
| NP2276 | Mm | 4 | 2 | 4 | 4 | 4 | 100 | 2 |

Table 3 shows a comparison between G07-NPXA6496 and a comparable inbred. G07-NPXA6496 has similar yield to NP2115. However, the present invention does require significantly less heat units to reach 50% silk.

Table 4 shows the GCA (General Combining Ability) estimates of G07-NPXA6496 compared with the GCA estimates of the other inbreds. The estimates show the general combining ability weighted by the second parent, or the number of experiment/location combinations or in which the specific hybrid combination occurs. The interpretation of the data for all traits is that a positive comparison is a practical advantage. A negative comparison is a practical disadvantage. The general combining ability of an inbred is clearly evidenced by the results of the general combining ability estimates. This data compares the inbred parent in a number of hybrid combinations to a group of "checks". The check data is from our company's and other companies' hybrids which are commercial products and pre-commercial hybrids, which were grown in the same sets and locations.

TABLE 3

PAIRED INBRED COMPARISON DATA

| Inbred | Yield | Stand | Heat Units to P50 | Heat Units to S50 | Plant Height | Ear Height | % Emergence | Warm Germ |
|---|---|---|---|---|---|---|---|---|
| G07-NPXA6496 | 108.8 | 33250.0 | 1377.7 | 1384.8 | 80.8 | 34.4 | 87.2 | 97.50 |
| NP2115 | 97.3 | 33900.0 | 1373.3 | 1350.8 | 76.4 | 38.6 | 89.5 | 99.00 |
| Diff | 6.9 | 1200.0 | 14.0 | 31.8 | 4.4 | 4.2 | 2.2 | 1.50 |
| #Expts | 5.0 | 5.0 | 6.0 | 5.0 | 5.0 | 5.0 | 7.0 | 2.00 |
| Prob | 0.4 | 0.5 | 0.6 | 0.039** | 0.2 | 0.2 | 0.2 | 0.21 |

| Inbred | % Discard | % Large Rounds | % Large Flats | % Med. Rounds | % Med. Flats | % Small Rounds | % Small Flats | Cold Germ |
|---|---|---|---|---|---|---|---|---|
| G07-NPXA6496 | 2.3 | 19.0 | 10.0 | 42.3 | 23.7 | 1.3 | 1.4 | 93.00 |
| NP2115 | 2.8 | 19.8 | 23.3 | 28.6 | 24.2 | 0.5 | 0.8 | 95.50 |
| Diff | 0.5 | 3.1 | 12.5 | 12.3 | 2.3 | 0.9 | 0.7 | 2.50 |
| #Expts | 5.0 | 5.0 | 5.0 | 5.0 | 5.0 | 5.0 | 5.0 | 2.00 |
| Prob | 0.4 | 0.6 | 0.041** | 0.030** | 0.7 | 0.054* | 0.1 | 0.34 |

*.05 < Prob <= .10

**.01 < Prob <= .05

***.00 < Prob <= .01

TABLE 4

| Parent 1 | Parent 2 | N05 | N06 | N | Yield | Moisture | Test Weight | % Stalk Lodging | % Late Root Lodging | % Early Root Lodging | % Dropped Ears |
|---|---|---|---|---|---|---|---|---|---|---|---|
| G07-NPXA6496 | | 25 | 30 | 55 | 9.9 | −1.8 | −1.6 | 2.7 | 1.7 | −2.7 | 0.0 |
| | XR = | 25 | 30 | 65 | 9.9 | −1.8 | −1.6 | 2.7 | 1.7 | −2.7 | 0.0 |
| | XH = | 25 | 30 | 1 | 9.9 | −1.8 | −1.6 | 2.7 | 1.7 | −2.7 | 0.0 |
| | XT = | 25 | 30 | 1 | 9.9 | −1.8 | −1.6 | 2.7 | 1.7 | −2.7 | 0.0 |

| Parent 1 | Parent 2 | N05 | N06 | N | Final Stand | % Stay Green | % Green Snap | Emergence Rating | Vigor Rating | Heat units to S50 | Heat units to P50 | Ear Height | Plant Height |
|---|---|---|---|---|---|---|---|---|---|---|---|---|---|
| G07-NPXA6496 | | 25 | 30 | 55 | −0.7 | 30.2 | −1.2 | −0.5 | 0.0 | 0.8 | −5.7 | 11.2 | 14.5 |
| | XR = | 25 | 30 | 65 | −0.7 | 30.2 | −1.2 | −0.5 | 0.0 | 0.8 | −5.7 | 11.2 | 14.5 |
| | XH = | 25 | 30 | 1 | −0.7 | 30.2 | −1.2 | −0.5 | 0.0 | 0.8 | −5.7 | 11.2 | 14.5 |
| | XT = | 25 | 30 | 1 | −0.7 | 30.2 | −1.2 | −0.5 | 0.0 | 0.8 | −5.7 | 11.2 | 14.5 |

XR = GCA Estimate: Weighted by Expt
XH = GCA Estimate: Weighted by Parent 2
XT = Same as XH but using only those parent 2 with two years of data Table 5A shows the inbred G07-NPXA6496 in hybrid combination, as Hybrid 1, in comparison with another hybrid, designated Hybrid 2, which is adapted for the same region of the Corn Belt. When in this hybrid combination, the present invention carries similar yield but significantly more moisture in comparison to the other commercial hybrid. The test weight, stand, percent stay green and the plant and ear height for the commercial hybrid and the present invention are also significantly different.

Table 5B shows the inbred G07-NPXA6496 in hybrid combination, as Hybrid 1, in comparison with another hybrid, designated Hybrid 3, which is adapted for the same region of the Corn Belt. When in this hybrid combination, the present invention carries similar yield, significantly more moisture, and significantly less test weight in comparison to the other commercial hybrid. The stalk logde and root lodge data also are significantly different as are a number of other traits.

TABLE 5A

PAIRED HYBRID COMPARISON DATA
Plot Data

| Hybrid | Yield | Moist | TWT | PCTERL | PCTSL | PCTPUSH |
|---|---|---|---|---|---|---|
| Hybrid 1 | 207.5 | 21.6 | 55.2 | 21.9 | 2.3 | 0.0 |
| Hybrid 2 | 202.3 | 20.3 | 55.8 | 0.0 | 1.5 | 10.0 |
| # Expts | 69.0 | 70.0 | 58.0 | 2.0 | 40.0 | 3.0 |
| Diff | 5.2 | 1.3 | 0.6 | 21.9 | 0.8 | 10.0 |
| Prob | 0.1 | 0.000*** | 0.000*** | 0.5 | 0.5 | 0.2 |

| Hybrid | PLTLRL | PCTDE | Stand | PCTSG | PCTGS | PctBarren |
|---|---|---|---|---|---|---|
| Hybrid 1 | 6.7 | 0.0 | 58.7 | 63.3 | 0.3 | 2.4 |
| Hybrid 2 | 7.1 | 0.0 | 60.8 | 38.3 | 1.3 | 0.0 |
| # Expts | 30.0 | 11.0 | 72.0 | 6.0 | 8.0 | 2.0 |
| Diff | 0.4 | 0.0 | 2.1 | 25.0 | 1.0 | 2.4 |
| Prob | 0.8 | | 0.005*** | 0.005*** | 0.4 | 0.5 |

| Hybrid | Emerge | Vigor | HUS50 | HUP50 | Pltht | Earht |
|---|---|---|---|---|---|---|
| Hybrid 1 | 3.5 | 3.9 | 1317.0 | 1322.0 | 296.5 | 120.9 |
| Hybrid 2 | 4.5 | 3.9 | 1317.0 | 1323.0 | 278.7 | 114.1 |
| # Expts | 4.0 | 10.0 | 5.0 | 5.0 | 9.0 | 10.0 |
| Diff | 1.0 | 0.0 | 0.0 | 0.4 | 17.7 | 6.8 |
| Prob | 0.2 | 1.0 | | 1.0 | 0.001*** | 0.016** |

*.05 < Prob <= .10
**.01 < Prob <= .05
***.00 < Prob <= .01

TABLE 5B

PAIRED HYBRID COMPARISON DATA

| Hybrid | Yield | Moist | TWT | PCTERL | PCTSL | PCTPUSH | PLTLRL |
|---|---|---|---|---|---|---|---|
| Hybrid 1 | 201.5 | 22.4 | 54.5 | 21.9 | 1.0 | 0.0 | 7.8 |
| Hybrid 3 | 197.4 | 21.5 | 55.1 | 0.0 | 2.3 | 30.0 | 1.1 |
| # Expts | 94.0 | 95.0 | 79.0 | 2.0 | 47.0 | 3.0 | 36.0 |
| Diff | 4.1 | 0.9 | 0.6 | 21.9 | 1.2 | 30.0 | 6.8 |
| Prob | 0.1 | 0.000*** | 0.000*** | 0.5 | 0.009*** | 0.4 | 0.002*** |

| Hybrid | PCTDE | Stand | PCTSG | PCTGS | PctBarren | Emerge | Vigor |
|---|---|---|---|---|---|---|---|
| Hybrid 1 | 0.0 | 59.6 | 63.3 | 0.3 | 2.4 | 4.3 | 3.9 |
| Hybrid 3 | 0.0 | 62.0 | 26.7 | 1.9 | 0.0 | 4.2 | 3.1 |
| # Expts | 13.0 | 97.0 | 6.0 | 8.0 | 2.0 | 6.0 | 10.0 |
| Diff | 0.0 | 2.4 | 36.7 | 1.6 | 2.4 | 0.2 | 0.8 |
| Prob | | 0.000*** | 0.002*** | 0.2 | 0.5 | 0.6 | 0.2 |

| Hybrid | HUS50 | HUP50 | Pltht | Earht |
|---|---|---|---|---|
| Hybrid 1 | 1317.0 | 1322.0 | 294.0 | 122.7 |
| Hybrid 3 | 1322.0 | 1311.0 | 270.5 | 108.5 |
| # Expts | 5.0 | 5.0 | 12.0 | 13.0 |
| Diff | 5.2 | 11.2 | 23.5 | 14.2 |
| Prob | 0.6 | 0.2 | 0.000*** | 0.000*** |

\*.05 < Prob <= .10
\*\*.01 < Prob <= .05
\*\*\*.00 < Prob <= .01

Table 6 shows the yield response of G07-NPXA6496 in hybrid combination, designated as Hybrid 1, in comparison with Hybrid 2 and 3 and the plants in the environment around it at the same location. The data for the present inbred is showing results that are within the error in the strip trials. In the plot trials the differences between the environment and the present invention was in each instance a bigger difference than the error would account for. However, the trend line for the strip plots is that the present invention is yielding very close to the level of the yield potential of that environment.

TABLE 6

YIELD RESPONSE

Research Plots

| Hybrid | Error | # Plots | 75 | 100 | 125 | 150 | 175 | 200 |
|---|---|---|---|---|---|---|---|---|
| Hybrid 2 | 18.9 | 77 | 82 | 110 | 138 | 165 | 193 | 221 |
| Hybrid 1 | 18.5 | 95 | 98 | 123 | 148 | 172 | 197 | 222 |
| Hybrid 3 | 17.4 | 102 | 102 | 125 | 148 | 170 | 193 | 216 |
| Hybrid 1 | 18.5 | 95 | 98 | 123 | 148 | 172 | 197 | 222 |

Strip Tests

| Hybrid | Error | # Strips | 75 | 100 | 125 | 150 | 175 | 200 |
|---|---|---|---|---|---|---|---|---|
| Hybrid 2 | 19.4 | 1473 | 82 | 107 | 131 | 155 | 180 | 204 |
| Hybrid 1 | 20.9 | 217 | 85 | 110 | 134 | 158 | 182 | 207 |
| Hybrid 3 | 23 | 437 | 85 | 109 | 133 | 156 | 180 | 204 |
| Hybrid 1 | 20.9 | 217 | 85 | 110 | 134 | 158 | 182 | 207 |

This invention also is directed to methods for producing a corn plant by crossing a first parent corn plant with a second parent corn plant wherein the first or second parent corn plant is an inbred corn plant from the line G07-NPXA6496. Further, both first and second parent corn plants can come from the inbred corn line G07-NPXA6496 which produces a self of the inbred invention. The present invention can be employed in a variety of breeding methods which can be selected depending on the mode of reproduction, the trait, and the condition of the germplasm. Thus, any breeding methods using the inbred corn line G07-NPXA6496 are part of this invention: selfing, backcrosses, hybrid production, and crosses to populations, and haploid by such old and known methods of using KWS inducers lines, Krasnador inducers, stock six material that induces haploids for dihaploid formation, and anther culturing and the like.

The present invention may be useful as a male-sterile plant. Sterility can be produced by pulling or cutting tassels from the plant, detasseling, use of gametocides, use of genetic material to render the plant sterile using a CMS type of genetic control or a nuclear genetic sterility. Male sterility is employed in a hybrid production by eliminating the pollen from the seed producing parent so when in isolation from other pollen source the only available pollen is that from the second male fertile inbred planted most often in rows near the male sterile inbred.

A number of different inventions exist which are designed to avoid detasseling in maize hybrid production. Some examples are switchable male sterility, lethal genes in the pollen or anther, inducible male sterility, male sterility genes with chemical restorers, sterility genes linked with a parent. U.S. Pat. No. 6,025,546, relates to the use of tapetum-specific promoters and the barnase gene. U.S. Pat. No. 6,627,799 relates to modifying stamen cells to provide male sterility. Therefore, one aspect of the current invention concerns the present invention comprising one or more gene(s) capable of restoring male fertility to male-sterile maize inbreds or hybrids.

Methods for genetic male sterility are disclosed in EPO 89/3010153.8, WO 90/08828, U.S. Pat. Nos. 4,654,465, 4,727,219, 3,861,709, 5,432,068 and 3,710,511. Gametocides which are chemicals or substances that negatively affect the pollen or at least the fertility of the pollen can be employed to provide male sterility.

Unfortunately for hybrid production nature complicates male sterility and as a result there are self pollinated female inbred seeds in some hybrid production. Great measures are taken to avoid this inbred production in a hybrid field but it unfortunately does occur. If a hybrid bag of seed is tested with molecular markers it may be possible to detect inbred seed. If the hybrid seed is planted these inbred plants tend to be readily identifiable by this runt like appearance—shorter plant, small ear. Self pollination of plants grown from these female inbreds seed produces the female inbred seed. This seed is not intended to be sold to the growers for breeding but only for use as grain and forage.

The process for producing inbred seed from a hybrid seed bag comprises planting a group of seed comprising seed from a hybrid production, one of the hybrid parents is the present invention, growing plants from this seed, identifying any inbred plants, selecting and pollinating the inbred plant.

A number of well known methods can be employed to identify the genotype of maize. The ability to understand the genotype of the present invention increases as the technology moves toward better markers for identifying different components within maize genetic material. One of the oldest methods is the use of isozymes which provides a generalized footprint of the material. Other markers that were adapted to provide a higher definition profile include Restriction Fragment Length Polymorphisms (RFLPs), Amplified Fragment Length Polymorphisms (AFLPs), Random Amplified Polymorphic DNAs (RAPDs), Polymerase Chain Reaction (there are different types of primers or probes) (PCR), Microsattelites (SSRs), and Single Nucleotide Polymorphisms (SNPs) just to list a few. The use of these and a number of other markers for gathering genotype information is well understood in the industry and can be found in college textbooks such as Breeding Field Crops, Milton et. al. Iowa State University Press.

The profile of the inbred of this invention should be close to homozygous for alleles. A marker profile produced with any of the locus identifying systems known in the industry will identify a particular allele at particular loci. A F1 hybrid made from the inbred of this invention will comprise a marker profile of the sum of both of its inbred parents. At each locus the allele for the present invention and the allele for the other inbred parent should be present. Thus the profile of the present invention will permit identification of hybrids as containing the inbred parent of the present invention. To identify the female portion of the hybrid the material from the pericarp which is maternally inherited is employed. The comparison of this maternal profile with the hybrid profile will allow identification of the paternal profile. The present invention includes a maize cell that is part of an inbred or hybrid plant which includes its seed or plant part that has the marker profile of alleles of the present invention.

Marker systems are not just useful for identification of the present invention; they are also useful for breeding and trait conversion techniques. Polymorphisms in maize permit the use of markers for linkage analysis. If SSR are employed with flanking primers PCR can be used and Southern Blots can often be eliminated. Use of flanking markers and PCR and amplification of the material is well known by the industry. Primers for SSRS and mapping information are publicly available through the help of the USDA at Maize GDB on the web.

Marker profiles of this invention can identify essentially derived varieties or progeny developed with the inbred in its ancestry. This inbred may have progeny identified by having a molecular marker profile of at least 25%, to 40%, 45%, 50% to 80% (which includes each of the number between these two percentages), 81%, 82%, 83%, 84%, 85%, 86%, 87%, 88%, 89%, 90%, 91%, 92%, 93%, 94%, 95%, 96%, 97%, 98%, 99% genetic contribution of the present inbred invention, as measured by either percent identity or percent similarity.

The present invention may have a new locus or trait introgressed through direct transformation or backcrossing or marker assisted breeding. A backcross conversion or locus conversion both refer to a product of a backcrossing program.

DNA sequences are introduced through backcrossing (Hallauer et al. in Corn and Corn Improvement, Sprague and Dudley, Third Ed. 1998), with the invention utilized as the recurrent parent.

When the present inbred is used as a recurrent parent in a breeding program it is often referred to as backcrossing. Backcrossing is often employed to introgression a desired trait or trait(s), either transgenic or nontransgenic, into the recurrent parent. A plant may be selected with the trait or the desired locus in one or more backcrosses. If markers are employed to assist in selection the number of backcrosses needed to recover the recurrent parent with the desired trait or locus can be relatively few two or three. However, 3, 4, 5 or more backcrosses are often required to produce the desired inbred with the gene or loci conversion in place. The number of backcrosses needed for a trait introgression is often linked to the genetics of the trait. Multigenic traits, recessive alleles, unlinked traits, and how the traits are inherited all play a role in the number of backcrosses that may be necessary to achieve the desired backcross conversion of the inbred.

Dominant, single gene traits or traits with obvious phenotypic changes are particularly well managed in a backcrossing program. Prior to transformation and prior to markers backcrossing was employed since at least the 1950's to alter grain color, to move mutations into inbreds—such as sugary 2, waxy, amylose extender, dull, brittle, shrunken, sugary 1, waxy (wx), shrunken-2, In a book written by Hallauer entitled Corn and Corn Improvement, Sprague and Dudley, 3rd Ed. 1998 the basics of this type of crossing along with a number of other corn breeding methods such as recurrent or bulk or mass selection, pedigree breeding, open pollination breeding, marker assisted selection, double haploids development and breeding are taught. The ordinary corn breeder understands these breeding systems and how to apply them to the present invention therefore repetition of these breeding methods need not be listed within this application.

The backcrossing program is more complicated when the trait is a recessive gene. To determine the presence of the recessive gene often requires the use of additionally testing to determine if the trait has been transferred. Use of markers to detect the gene reduces the complexity of trait identification in the progeny. A marker that is a SNP specific for the trait itself can be very useful in increasing the efficiency and speed of tracking a recessive trait within a backcrossing program. Backcrossing of recessive traits has been preformed since at least the 1950 as mutant traits are often recessive. These mutant traits are frequently moved into more elite germplasm. Mutations can result from acts of nature or plant or seed or pollen exposure to temperature alterations, culturing, radiation in various forms, chemical mutagens like EMS and others. Some of the mutant genes which have been identified in maize include the genotypes: waxy (wx), amylose extender (ae), dull (du), horny (h), shrunken (sh), brittle (bt), floury (fl), opaque (o), and sugary (su). Nomenclature for mutant genes is based on the effect these mutant genes have on the physical appearance, phenotype, of the kernel. It is also known that within these genotypes there are genes which produce starch with markedly different functional properties even though the phenotypes are the same. Such subspecies have generally been given a number after the named genotype, for example, sugary-1), sugary-2 (su2); shrunken 1 and shrunken 2. Traits such as Ht, waxy, shrunken, amylose extender, opaque, sugary 1, 2, dull, IT (imidazolmone tolerance), IR, sterility, fertility, phytic acid, NLB (northern leaf blight), SLB (southern leaf blight), and the like have all been introgressed into elite inbreds through backcrossing programs. The last backcross generation is usually selfed if necessary to recover the inbred of interest with the introgressed trait.

All plants and plant cells produced using inbred corn line G07-NPXA6496 are within the scope of this invention. The invention encompasses the inbred corn line used in crosses with other, different, corn inbreds to produce (F1) corn hybrid seeds and hybrid plants and the grain produced on the hybrid plant. This invention includes plant and plant cells, which upon growth and differentiation produce corn plants having the physiological and morphological characteristics of the inbred line G07-NPXA6496.

Additionally, this maize can, within the scope of the invention, contain: transgenic genes such as but not limited to insect resistant genes such as European Corn Borer resistant gene(s), Corn Rootworm gene(s), an example is event DAS-59122-7, Mir603 Modified Cry3A event, MON 89034, MON 88017 Bacillus thuringiensis (Cry genes) Cry34/35Ab1, Cry1A.105, PO Cry1F, Cry2Ab2, Cry1A, Cry1AB, Cry1Ac, Cry3Bb1, or other Bt genes with resistance to other insects. Hherbicide resistant genes such as Pat gene or Bar gene, EPSP, the altered protoporphyrinogen oxidase (protox enzyme) U.S. Pat. Nos. 5,767,373, 6,282,837, WO 01/12825 and the like can be introduced into the present invention. And disease resistant genes such as the Mosaic virus resistant gene, etc., or trait altering genes such as lignin genes, flowering genes, oil modifying genes, senescence genes and the like can be introduced in combination with other genes to form stacks or individual. Altered carbohydrates or altered starch can include genes for enzymes that affects the synthase, branching enzymes, pullanases, debranching enzymes, isoamylases, alpha amylases, beta amylases, AGP, ADP and other enzymes which effect the amylose, amylopectin ratio or content or the branching pattern of starch are within the scope of this invention. The fatty acid modifying genes can also affect starch content and be introduced into the present invention.

The methods and techniques for inserting, or producing and/or identifying a mutation or making or reshuffling a transgene and introgressing the trait or gene into the present invention through breeding, transformation, mutating and the like are well known and understood by those of ordinary skill in the art.

Various techniques for breeding, moving or altering genetic material within or into the present invention (whether it is an inbred or in hybrid combination) are also known to those skilled in the art. These techniques to list only a few are anther culturing, haploid/double haploid production, (stock six, which is a breeding/selection method using color markers and is a haploid method that has been in use for forty years and is well known to those with skill in the art), transformation, irradiation to produce mutations, chemical or biological mutation agents and a host of other methods are within the scope of the invention. All parts of the G07-NPXA6496 plant including its plant cells (with maternal and paternal components) produced using the inbred corn line is within the scope of this invention. The term transgenic plant refers to plants having genetic sequences, which are introduced into the genome of a plant by a transformation method and the progeny thereof. The transgene once introduced into plant material and integrated stably can be moved into other germplasm by standard breeding practices.

The basic steps of introducing genes into monocots have been known in the art for years. The most common method of maize transformation is referred to as gunning or microprojectile bombardment. The process employs small gold-coated particles coated with DNA which are shot into the transformable material. Detailed techniques for gunning DNA into cells, tissue, callus, embryos, and the like are well known in the prior art. One example of steps that can be involved in monocot transformation are concisely outlined in U.S. Pat. No. 5,484,956 "Fertile Transgenic Zea mays Plants Comprising Heterologous DNA Encoding Bacillus Thuringiensis Endotoxin" issued Jan. 16, 1996 and also in U.S. Pat. No. 5,489,520 "Process of Producing Fertile Zea mays Plants and Progeny Comprising a Gene Encoding Phosphinothricin Acetyl Transferase" issued Feb. 6, 1996.

Plant cells such as maize can be transformed not only by the use of a gunning device but also by a number of different techniques. The recombinant DNA molecules of the invention can be introduced into the plant cell in a number of art-recognized ways. Those skilled in the art will appreciate that the choice of method might depend on the type of plant material being targeted for transformation. Suitable methods of transforming plant cells include microinjection (Crossway et al., BioTechniques 4:320-334 (1986)), electroporation (Riggs et al, Proc. Natl. Acad. Sci. USA 83:5602-5606 (1986), Agrobacterium mediated transformation (Hinchee et al., Biotechnology 6:915-921 (1988)), direct gene transfer (Paszkowski et al., EMBO J. 3:2717-2722 (1984)), ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., Biotechnology 6:923-926 (1988)), protoplast transformation/regeneration methods (see U.S. Pat. No. 5,350,689 issued Sep. 27, 1994 to Ciba-Geigy Corp.), Whiskers technology (See U.S. Pat. Nos. 5,464,765 and 5,302,523) and pollen transformation (see U.S. Pat. No. 5,629,183). Also see, Weissinger et al., Annual Rev. Genet. 22:421-477 (1988); Sanford et al., Particulate Science and Technology 5:27-37 (1987)(onion); Christou et al., Plant Physiol. 87:671-674 (1988)(soybean); McCabe et al., Bio/Technology 6:923-926 (1988)(soybean); Datta et al., Bio/Technology 8:736-740 (1990)(rice); Klein et al., Proc. Natl. Acad. Sci. USA, 85:4305-4309 (1988)(maize); Klein et al., Bio/Technology 6:559-563 (1988)(maize); Klein et al., Plant Physiol. 91:440-444 (1988)(maize); Fromm et al., Bio/Technology 8:833-839 (1990); Gordon-Kamm et al., Plant Cell 2:603-618 (1990) (maize); and U.S. Pat. Nos. 5,591,616 and 5,679,558 (rice), for more transformation information.

A further subject of the present invention is the plants regenerated from transformed cells. Regeneration is effected by any suitable process, which depends on the nature of the species are listed in these patents and patent applications which are cited in particular for the processes for transforming plant cells and regenerating plants are the following: U.S. Pat. Nos. 4,459,355, 4,536,475, 5,464,763, 5,177,010, 5,187,073, EP 267,159, EP 604 662, EP 672 752, U.S. Pat. Nos. 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253, 5,405,765, EP 442 174, EP 486 233, EP 486 234, EP 539 563, EP 674 725, WO 91/02071 and WO 95/06128.

The use of pollen, cotyledons, zygotic embryos, meristems and ovum as the target issue can eliminate the need for extensive tissue culture work. Generally, cells derived from meristematic tissue are useful. The method of transformation of meristematic cells of cereal is taught in the PCT application WO96/04392. Any number of various cell lines, tissues, calli and plant parts can and have been transformed by those having knowledge in the art. Methods of preparing meristems, callus or protoplasts from various plants are well known in the art and specific methods are detailed in patents and references used by those skilled in the art. The requirement of the plant material is that it can ultimately be used to form a transformed plant.

The DNA used for transformation of plants may be circular, linear, and double or single stranded. Usually, the DNA is in the form of a plasmid. The plasmid usually contains regulatory and/or targeting sequences which assists the expression or targeting of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense: multiple gene copies or artificial gene chromosomes can be used. The transgene can come from various non-plant genes (such as; bacteria, yeast, animals, and viruses) along with being from plants.

The regulatory promoters employed can be constitutive such as CaMv35S promoter, rice action promoter, and polyubiquitin promoter U.S. Pat. No. 5,614,399, for monocots or tissue specific promoters such as CAB promoters, MR7 described in U.S. Pat. No. 5,837,848, etc. The prior art promoters, includes but is not limited to, octopine synthase, nopaline synthase, CaMv19S, mannopine synthase, Figwort mosaic virus promoter, etc. These regulatory sequences can be combined with introns, terminators, enhancers, leader sequences and the like in the material used for transformation.

The isolated DNA is then transformed into the plant. A gene introgressed into this invention typically comprises a nucleotide sequence whose expression is responsible or contributes to the trait under the control of a promoter appropriate for the expression of the nucleotide sequence at the desired time in the desired tissue or part of the plant. Constitutive or inducible promoters are used. The sequence may also comprise other regulatory elements such as for example translation enhancers or termination signals. In an embodiment, the nucleotide sequence is the coding sequence of a gene and is transcribed and translated into a protein. In another embodiment, the nucleotide sequence encodes an antisense RNA, a sense RNA that is not translated or only partially translated, a t-RNA, a r-RNA or a sn-RNA.

The genes responsible for a specific gene trait are generally inherited through the nucleus. Known exceptions are, e.g. the genes for male sterility, some of which are inherited cytoplasmically, but still act as single gene traits. In an embodiment, a heterologous transgene is integrated into the nuclear genome of the donor, non-recurrent parent. In another embodiment, a heterologous transgene to be transferred to into present invention is integrated into the plastid genome of a donor, non-recurrent parent. In an embodiment, a plastid transgene comprises one gene transcribed from a single promoter or two or more genes transcribed from a single promoter.

In an other embodiment, a transgene whose expression results or contributes to a desired trait to be transferred to the present invention comprises a virus resistance trait such as, for example, a MDMV strain B coat protein gene whose expression confers resistance to mixed infections of maize dwarf mosaic virus and maize chlorotic mottle virus in transgenic maize plants (Murry et al. Biotechnology (1993) 11:1559 64).

In another embodiment, a transgene comprises a gene encoding an insecticidal protein, such as, for example, a crystal protein of *Bacillus thuringiensis* or a vegetative insecticidal protein from *Bacillus cereus*, such as VIP3 (see for example Estruch et al. Nat Biotechnol (1997) 15:137 41). Also see, U.S. Pat. Nos. 5,877,012, 6,291,156; 6,107,279 6,291,156 and 6,429,360. In another embodiment, an insecticidal gene introduced into the present invention is a Cry1Ab gene or a portion thereof, for example introgressed into present invention from a maize line comprising a Bt-11 event as described in U.S. Pat. No. 6,114,608, which is incorporated herein by reference, or from a maize line comprising a 176 event as described in Koziel et al. (1993) Biotechnology 11: 194 200. In yet another embodiment, a transgene introgressed into the present invention comprises a herbicide tolerance gene. For example, expression of an altered acetohydroxyacid synthase (AHAS) enzyme confers upon plants tolerance to various imidazolinone or sulfonamide herbicides (U.S. Pat. No. 4,761,373). In another embodiment, a non-transgenic trait conferring tolerance to imidazolinones is introgressed into present invention (e.g. a "IT" or "IR" trait). U.S. Pat. No. 4,975,374, relates to plant cells and plants containing a gene encoding a mutant glutamine synthetase (GS) resistant to inhibition by herbicides that are known to inhibit GS, e.g. phosphinothricin and methionine sulfoximine. Also, expression of a *Streptomyces* bar gene encoding a phosphinothricin acetyl transferase in maize plants results in tolerance to the herbicide phosphinothricin or glufosinate (U.S. Pat. No. 5,489,520). U.S. Pat. No. 5,013,659, which is incorporated herein by reference, is directed to plants that express a mutant acetolactate synthase (ALS) that renders the plants resistant to inhibition by sulfonylurea herbicides. U.S. Pat. No. 5,162, 602 discloses plants tolerant to inhibition by cyclohexanedione and aryloxyphenoxypropanoic acid herbicides. The tolerance is conferred by an altered acetyl coenzyme A carboxylase (ACCase). U.S. Pat. No. 5,554,798 discloses transgenic glyphosate tolerant maize plants, which tolerance is conferred by an altered 5-enolpyruvyl-3-phosphoshikimate (EPSP) synthase gene. U.S. Pat. No. 5,804,425 discloses transgenic glyphosate tolerant maize plants, which tolerance is conferred by an EPSP synthase gene derived from *Agrobacterium tumefaciens* CP-4 strain. Also, tolerance to a protoporphyrinogen oxidase inhibitor is achieved by expression of a tolerant protoporphyrinogen oxidase enzyme in plants (U.S. Pat. No. 5,767,373). Another trait transferable to the present invention confers a safening effect or additional tolerance to an inhibitor of the enzyme hydroxyphenylpyruvate dioxygenase (HPPD) and transgenes conferring such trait are, for example, described in WO 9638567, WO 9802562, WO 9923886, WO 9925842, WO 9749816, WO 9804685 and WO 9904021. All issued patents referred to herein are, in their entirety, expressly incorporated herein by reference.

In yet another embodiment, a transgene transferred to present invention comprises a gene conferring tolerance to a herbicide and at least another nucleotide sequence encoding at least one other trait, such as for example, an insecticidal protein. Such combination of single gene traits is for example a Cry1Ab gene and a bar gene.

By way of example only, specific events (followed by their APHIS petition numbers) that can be introduced into maize plants include the glyphosate tolerant event GA21 (97-09901p) or the glyphosate tolerant event NK603 (00-011-01p), the glyphosate tolerant/Lepidopteran insect resistant event MON 802 (96-31701p) Mon810, Lepidopteran insect resistant event DBT418 (96-29101p), male sterile event MS3 (95-22801p), Lepidopteran insect resistant event Bt11 (95-

19501p), phosphinothricin tolerant event B16 (95-14501p), Lepidopteran insect resistant event MON 80100 (95-09301p) and MON 863 (01-137-01p), phosphinothricin tolerant events T14, T25 (94-35701p), Lepidopteran insect resistant event 176 (94-31901p) and Western corn rootworm (04-362-01p), and the phosphinothricin tolerant and Lepidopteran insect resistant event CBH-351 (92-265-01p).

Maize is used as human food, livestock feed, and as raw material in industry. Sweet corn kernels having a relative moisture of approximately 72% are consumed by humans and may be processed by canning or freezing. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry. Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications. Plant parts other than the grain of maize are also used in industry: for example, stalks and husks are made into paper and wallboard and cobs are used for fuel and to make charcoal.

The present invention therefore also discloses an agricultural product comprising a plant of the present invention or derived from a plant of the present invention. The present invention also discloses an industrial product comprising a plant of the present invention or derived from a plant of the present invention. The present invention further discloses methods of producing an agricultural or industrial product comprising planting seeds of the present invention, growing plant from such seeds, harvesting the plants and processing them to obtain an agricultural or industrial product.

A deposit of at least 2500 seeds of this invention will be maintained by Syngenta Seed Inc. Access to this deposit will be available during the pendency of this application to the Commissioner of Patents and Trademarks and persons determined by the Commissioner to be entitled thereto upon request. All restrictions on availability to the public of such material will be removed upon issuance of a granted patent of this application by depositing at least 2500 seeds of this invention at the American Type Culture Collection (ATCC), at 10801 University Boulevard, Manassas, Va. 20110. The ATCC number of the deposit is PTA-11201. The date of deposit was Jul. 16, 2010 and the seed was tested on Aug. 2, 2010 and found to be viable. The deposit of at least 2500 seeds will be from inbred seed taken from the deposit maintained by Syngenta Seed Inc. The ATCC deposit will be maintained in that depository, which is a public depository, for a period of 30 years, or 5 years after the last request, or for the enforceable life of the patent, whichever is longer, and will be replaced if it becomes nonviable during that period.

Additional public information on plant variety protection may be available from the PVP Office, a division of the U.S. Government.

The present invention encompasses a method of producing treated hybrid or inbred seed of the present invention and the resultant treated seed. The method includes obtaining seed and treating the seed to improve its performance. Hybrid and inbred seed is often treated with one or more pesticides including fungicides, herbicides, herbicidal safeners, fertilizers, insecticides, acaricides, nematocides, bactericides, virus resistant material and other biocontrol agents. Pyrethrins, synthetic pyrethroids, oxadizine derivatives, chloronicotinyls, nitroguanidine derivatives and triazoles, organophosphates, pyrrols, pyrazoles, phenyl pyrazoles, diacylhydrazines, biological/fermentation products and carbamates are used as pesticidal seed treatments. Additionally, Fludioxonil, mefenoxam, azoxystrobin, thiamethoxam, clothianidin and the like are frequently used to treat maize seed. Methods for treating seed using fluidized beds, roller mills, rotostatic seed treater and drum coaster, misting, soaking, filming coating and the like. These methods of seed treatment are well known in the industry.

The present invention encompasses a hybrid plant with a plant part being the segregating grain formed on the ear of the hybrid. This grain is a commodity plant product as are the protein concentrate, protein isolate, starch, meal, flour or oil. A number of different industrial processes extract or utilize these plant products.

Accordingly, the present invention has been described with some degree of particularity directed to the embodiment of the present invention. It should be appreciated, though that the present invention is defined by the following claims construed in light of the prior art so that modifications or changes may be made to the embodiment of the present invention without departing from the inventive concepts contained herein.

What is claimed is:

1. A seed of the maize inbred plant G07-NPXA6496, representative seed of said plant having been deposited under ATCC Accession Number PTA-11201.

2. A maize inbred plant G07-NPXA6496, representative seed according to claim 1 of said G07-NPXA6496 plant having been deposited under ATCC Accession Number PTA-11201.

3. A plant part of the plant of claim 2.

4. The plant part of claim 3, wherein said part is pollen, protoplast, cell, tassel, anther or an ovule.

5. A maize seed comprising the plant part of claim 3 wherein said plant part is said cell.

6. A process for producing an F1 hybrid maize seed, said process comprising crossing the plant of maize inbred plant G07-NPXA6496 according to claim 2 with a different maize plant and harvesting the resultant F1 hybrid maize seed.

7. A maize plant or plant part produced by growing the F1 hybrid maize seed of claim 6.

8. An F1 hybrid maize seed obtained by the method of crossing the plant of claim 2 with another, different maize plant, whereby the plant of claim 2 is the female parent.

9. A method for producing maize seed comprising growing the plant of claim 2 until seed is produced, harvesting the seed, wherein the harvested seed is inbred or hybrid.

10. A seed produced by the method of claim 9.

11. A process of introducing a desired trait into maize inbred plant G07-NPXA6496 comprising: (a) crossing G07-NPXA6496 plants grown from G07-NPXA6496 seed, representative seed of which has been deposited under ATCC Accession Number PTA-11201, with plants of another maize plant that comprise a desired trait to produce F1 progeny plants, wherein the desired trait is selected from the group consisting of waxy starch, male sterility, herbicide resistance, altered starch, insect resistance, bacterial disease resistance, fungal disease resistance, and viral disease resistance; (b) selecting F1 progeny plants that have the desired trait to produce selected F1 progeny plants; (c) crossing the selected progeny plants with the G07-NPXA6496 plants to produce backcross progeny plants; (d) selecting for backcross progeny plants that have the desired trait to produce selected backcross progeny plants; and (e) repeating steps (c) and (d) at least three or more times to produce backcross progeny plants that comprise the desired trait and all of the physiological and morphological characteristics of maize inbred plant G07-NPXA6496 listed in Table 1 when grown in the same environmental conditions.

12. A plant produced by the process of claim 11.

13. A maize plant having all the physiological and morphological characteristics of inbred plant G07-NPXA6496, wherein a sample of the seed of inbred plant G07-NPXA6496 was deposited under ATCC Accession Number PTA-11201.

14. The maize plant of claim 11, further defined as having a genome comprising at least one transgene or a trait conferred by a transgene.

15. The maize plant of claim 14, wherein the transgene confers a trait selected from the group consisting of herbicide tolerance; insect tolerance; resistance to bacterial, fungal, nematode or viral disease; waxy starch; altered starch, male sterility and restoration of male fertility, modified carbohydrate metabolism or modified fatty acid metabolism.

16. A method of producing a maize plant derived from the inbred plant G07-NPXA6496, the method comprising the steps of (a) growing a progeny plant produced by crossing the plant of claim 2 with a second maize plant; (b) crossing the progeny plant with itself or a different plant to produce a seed of a progeny plant of a subsequent generation; (c) growing a progeny plant of a subsequent generation from said seed and crossing the progeny plant of a subsequent generation with itself or a different plant; and (d) repeating steps (b) and (c) for an additional 0-5 generations to produce a maize plant derived from the inbred plant G07-NPXA6496.

17. A method for developing a maize plant in a maize plant breeding program, comprising applying plant breeding techniques comprising recurrent selection, backcrossing, pedigree breeding, marker enhanced selection, haploid/dihaploid production, and transformation to the maize plant of claim 2, or its parts, wherein application of said techniques results in development of a maize plant.

18. A method of producing a commodity plant product comprising growing the plant from the seed of claim 10 or a part thereof and producing said commodity plant product comprising protein concentrate, protein isolate, starch, meal, flour or oil therefrom.

19. A method of producing a treated seed comprising obtaining the seed of claim 10 and treating said seed.

* * * * *